(12) United States Patent
Schubert

(10) Patent No.: US 7,244,845 B2
(45) Date of Patent: Jul. 17, 2007

(54) PROCESS FOR PREPARING CYCLIC N-SUBSTITUTED ALPHA-IMINO CARBOXYLIC ACIDS

(75) Inventor: Gerrit Schubert, Kelkheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 273 days.

(21) Appl. No.: 10/981,120

(22) Filed: Nov. 4, 2004

(65) Prior Publication Data

US 2005/0131231 A1 Jun. 16, 2005

Related U.S. Application Data

(60) Provisional application No. 60/551,437, filed on Mar. 9, 2004.

(30) Foreign Application Priority Data

Nov. 6, 2003 (DE) ................. 103 51 904

(51) Int. Cl.
  C07D 471/00 (2006.01)
  C07D 487/00 (2006.01)
  C07D 217/22 (2006.01)
  C07C 303/00 (2006.01)
  C07C 307/00 (2006.01)

(52) U.S. Cl. ............ 544/350; 546/113; 546/118; 546/122; 546/141; 560/12; 560/27

(58) Field of Classification Search ............ None
See application file for complete search history.

(56) References Cited

U.S. PATENT DOCUMENTS

| | | | | |
|---|---|---|---|---|
| 3,674,878 | A * | 7/1972 | Degginger et al. | 424/330 |
| 6,207,672 | B1 | 3/2001 | Thorwart et al. | |
| 6,573,277 | B2 | 6/2003 | Thorwart et al. | |
| 6,716,853 | B2 * | 4/2004 | Stahl et al. | 514/303 |
| 6,815,440 | B2 | 11/2004 | Thorwart et al. | |

FOREIGN PATENT DOCUMENTS

NL  1700467  *  4/1967

OTHER PUBLICATIONS van Gelderen, "Reactions of 4-biphenyl isocyanate with alcohols and amino compounds" Recueil des Travaux Chimiques des Pay-Bays et de la Belgique, vol. 52, pp. 969-975 (1933) as Abstracted by STN-Caplus.*
Morgan et al, "Production of higher alcohols, aldehydes and ketones" Chemistry & Industry, pp. 518-519 (1933). as Abstracted by STN-Caplus.*
Simonsen and Gillam, "α-Cyperone, a sesquiterpene ketone from the oil of *Cyperus rotundus*" Journal of the Chemical Society, pp. 667-677 (1936) as Abstracted by STN-Caplus.*
Kenyon and Young, "Constitution of the alcohol (δ-methyl-δ-penten-β-ol) previously resolved and described as α,γ,γ-trimethylallyl alcohol" Journal of the Chemical Society, pp. 1452-1454 (1938) as Abstracted by STN-Caplus.*
Arcus and Kenyon, "Reduction of the carbonyl group in unsaturated ketones and the interconversion of geometrical isomerides during such reduction" Journal of the Chemical Society, pp. 698-699 (1938) as Abstracted by STN-Caplus.*
Kenyon and Young, "Composition of the Ponndorff-Meerwein reduction product of mesityl oxides" Journal of the Chemical Society, pp. 1547-1550 (1940) as Abstracted by STN-Caplus.*
Crombie and Harper, "Synthesis and configuration of (+)-6-methyloctanoic acid, a degradation product of the polymyxins" Journal of the Chemical Society, pp. 2685-2689 (1950) as Abstracted by STN-Caplus.*
Crombie and Harper, "'Leaf alcohol' and the stereochemistry of the cis- and trans-3-hexen-1-ols and -3-penten-1-ols" Journal of the Chemical Society, pp. 873-877 (1950) as Abstracted by STN-Caplus.*
Crombie, "Amides of vegetable origin. I. Stereoisomeric N-isobutyl-1,7-hendecadien-1-carboxyamides and the structure of herculin" Journal of the Chemical Society, pp. 2997-3008 (1952) as Abstracted by STN-Caplus.*
Crombie, "Amides of vegetable origin. II. Stereoisomeric N-isobutyl-1,5-nonadien-1-carboxamides and the structure of pellitorine" Journal of the Chemical Society, pp. 4338-4346 (1952) as Abstracted by STN-Caplus.*
van Gelderen, "Reactions of 4-biphenyl isocyanate with alcohols and amino compounds" Recueil des Travaux Chimiques des□□ Pay-Bays et de la Belgique, vol. 52, pp. 969-975 (1933).*
Morgan et al, "Production of higher alcohols, aldehydes and ketones" Chemistry & Industry, pp. 518-519 (1933).□□.*
Simonsen and Gillam, "α-Cyperone, a sesquiterpene ketone from the oil of *Cyperus rotundus*" Journal of the Chemical Society,□□pp. 667-677 (1936).*
Kenyon and Young, "Constitution of the alcohol (5-methyl-6-penten-13-ol) previously resolved and described as α,γ,γ-trimethylallyl alcohol" Journal of the Chemical Society, pp. 1452-1454 (1938).*
Arcus and Kenyon, "Reduction of the carbonyl group in unsaturated ketones and the interconversion of geometrical isomerides during such reduction" Journal of the Chemical Society, pp. 698-699 (1938).*
Kenyon and Young, "Composition of the Ponndorff-Meerwein reduction product of mesityl oxides" Journal of the Chemical Society, pp. 1547-1550 (1940).*

(Continued)

*Primary Examiner*—Zachary C. Tucker
(74) *Attorney, Agent, or Firm*—Ronald G. Ort

(57) ABSTRACT

The present invention relates to the novel methods of making matrix metalloproteinase inhibitors of Formula (I):

(I)

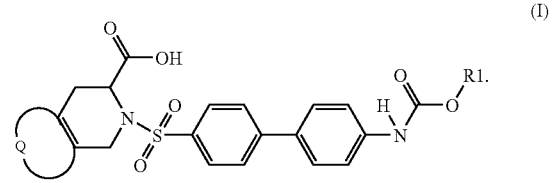

23 Claims, No Drawings

OTHER PUBLICATIONS

Crombie and Harper, "Synthesis and configuration of (+)-6-methyloctanoic acid, a degradation product of the polymyxins" Journal of the Chemical Society, pp. 2685-2689 (1950).*

Crombie and Harper, "'Leaf alcohol' and the stereochemistry of the cis- and trans-3-hexen-I-ols and -3-penten-I-ols" Journal of the Chemical Society, pp. 873-877 (1950).*

Crombie, "Amides of vegetable origin. I. Stereoisomeric N-isobutyl-l,7-hendecadien-I-carboxyamides and the structure of herculin" Journal of the Chemical Society,.pp. 2997-3008 (1952).*

Crombie, "Amides of vegetable origin. II. Stereoisomeric N-isobutyl-l,5-nonadien-I-carboxamides and the structure of pellitorine" Journal of the Chemical Society, pp. 4338-4346 (1952).*

Greene, et al., Silyl Esters, Protective Groups in Organic Chemistry; Wiley, New York, 1991; Chapter 5; pp. 261-263.

Larock, R.C., Interconversion of Nitriles, Carboxylic Acids and Derivatives, Comprehensive Organic Transformations: A Guide to Functional Group Preparations, VCH Publishers, New York, Weinheim; 1999; pp. 1929-1930.

March, et al., Aromatic Electrophilic Substitution, March's Advanced Organic Chemistry: Reactions, Machanisms, adn Structure; Wiley, New York, 2001; pp. 702-704.

* cited by examiner

PROCESS FOR PREPARING CYCLIC N-SUBSTITUTED ALPHA-IMINO CARBOXYLIC ACIDS

RELATED APPLICATIONS

This Application is based on and claims priority under 35 U.S.C. § 119(e) to U.S. provisional patent application Ser. No. 60/551,437, filed on Mar. 9, 2004, which is incorporated herein by reference. This Application is also based on and claims priority under 35 U.S.C. § 119(a) to Federal Republic of Germany patent application No. 10351904.1, filed on Nov. 6, 2003, which is incorporated herein by reference.

FIELD OF THE INVENTION

This Application relates to a process for preparing certain cyclic and heterocyclic N-substituted alpha-imino hydroxamic and carboxylic acids according to Formula (I) that are useful as matrix metalloproteinase inhibitors in the treatment of conditions characterized by over-expression and activity of matrix metalloproteinase.

BACKGROUND OF THE INVENTION

The matrix metalloproteinases (MMP's) are a family of zinc containing endopeptidases which are capable of cleaving large biomolecules such as the collagens, proteoglycans and gelatins. Expression is upregulated by pro-inflammatory cytokines and/or growth factors. The MMP's are secreted as inactive zymogens which, upon activation, are subject to control by endogenous inhibitors, for example, tissue inhibitor of metalloproteinases (TIMP) and $\alpha_2$-macroglobulin. Chapman, K. T. et al., *J. Med. Chem.* 36, 4293–4301 (1993); Beckett, R. P. et al., *DDT* 1, 16–26 (1996). The characterizing feature of diseases involving the enzymes appears to be a stoichiometric imbalance between active enzymes and endogenous inhibitors, leading to excessive tissue disruption, and often degradation. McCachren, S. S., *Arthritis Rheum.* 34, 1085–1093 (1991).

The discovery of different families of matrix metalloproteinase, their relationships, and their individual characteristics have been categorized in several reports. Emonard, H. et al., *Cell Molec. Biol.* 36, 131–153 (1990); Birkedal-Hansen, H., *J. Oral Pathol.* 17, 445–451 (1988); Matrisian, L. M., *Trends Genet.* 6, 121–125 (1990); Murphy, G. J. P. et al., *FEBS Lett.* 289, 4–7 (1991); Matrisian, L. M., *Bioessays* 14, 455–463 (1992). Three groups of MMPs have been delineated: the collagenases which have triple helical interstitial collagen as a substrate, the gelatinases which are proteinases of denatured collagen and Type IV collagen, and the stromelysins which were originally characterized as proteoglycanases but have now been identified to have a broader proteolytic spectrum. Examples of specific collagenases include fibroblast collagenase characterized as proteoglycanases but have now been identified to have a broader proteolytic spectrum. Examples of specific collagenases include fibroblast collagenase (MMP-1), neutrophil collagenase (MMP-8), and collagenase 3 (MMP-13). Examples of gelatinases include 72 kDa gelatinase (gelatinase A; MMP-2) and 92 kDa gelatinase (gelatinase B; MMP-9). Examples of stromelysins include stromelysin 1 (MMP-3), stromelysin 2 (MMP-10) and matrilysin (MMP-7). Other MMPs which do not fit neatly into the above groups include metalloelastase (MMP-12), membrane-type MMP (MT-MMP or MMP-14) and stromelysin 3 (MMP-11). Beckett, R. P. et al., supra.

Over-expression and activation of MMPs have been linked with a wide range of diseases such as cancer; rheumatoid arthritis; osteoarthritis; chronic inflammatory disorders, such as, for example, emphysema; cardiovascular disorders, such as, for example, atherosclerosis; corneal ulceration; dental diseases such as, for example, gingivitis; periodontal disease; neurological disorders, such as, for example, multiple sclerosis; and smoking-induced emphysema.

For example, in adenocarcinoma, invasive proximal gastric cells express the 72 kDa form of collagenase Type IV, whereas the noninvasive cells do not. Schwartz, G. K. et al., *Cancer* 73, 22–27 (1994). Rat embryo cells transformed by the Ha-ras and v-myc oncogenes or by Ha-ras alone are metastatic in nude mice and release the 92 kDa gelatinase/collagenase (MMP-9). Bernhard, E. J. et al., *Proc. Natl. Acad. Sci.* 91, 4293–4597 (1994). The plasma concentration of MMP-9 was significantly increased (P<0.01) in 122 patients with gastrointestinal tract cancer and breast cancer. Zucker, S. et al., *Cancer Res.* 53, 140–146 (1993). Moreover, intraperitoneal administration of batimastat, a synthetic MMP inhibitor, gave significant inhibition in the growth and metastatic spread and number of lung colonies that were produced by intravenous injection of the B16-BL6 murine melanoma in C57BL/6N mice. Chirivi, R. G. S. et al., *Int. J. Cancer* 58, 460–464 (1994). Over-expression of TIMP-2, the endogenous tissue inhibitor of MMP-2, markedly reduced melanoma growth in the skin of immunodeficient mice. Montgomery, A. M. P. et al., *Cancer Res.* 54, 5467–5473 (1994).

Accelerated breakdown of the extracellular matrix of articular cartilage is a key feature in the pathology of both rheumatoid arthritis and osteoarthritis. Current evidence suggests that the inappropriate synthesis of MMPs is the key event. Beeley, N. R. A. et al., *Curr. Opin. Ther. Patents*, 4(1), 7–16 (1994). The advent of reliable diagnostic tools have allowed a number of research groups to recognize that stromelysin is a key enzyme in both arthritis and joint trauma. Beeley, N. R. A. et al., Id.; Hasty, K. A. et al., *Arthr. Rheum.* 33, 388–397 (1990). It has also been shown that stromelysin is important for the conversion of procollagenase to active collagenase. Murphy, G. et al., *Biochem. J.* 248, 265–268 (1987).

Furthermore, a range of MMPs can hydrolyse the membrane-bound precursor of the pro-inflammatory cytokine tumor necrosis factor .alpha. (TNF-$\alpha$). Gearing, A. J. H. et al., *Nature* 370, 555–557 (1994). This cleavage yields mature soluble TNF-$\alpha$ and the inhibitors of MMPs can block production of TNF-$\alpha$ both in vitro and in vivo. Gearing, A. J. H. et al., Id.; Mohler, K. M. et al., *Nature* 370, 218–220 (1994); McGeehan, G. M. et al., *Nature* 370, 558–561 (1994). This pharmacological action is a probable contributor to the antiarthritic action of this class of compounds seen in animal models. Beckett, R. P. et al., supra.

Stromelysin has been observed to degrade the $\alpha_1$-proteinase inhibitor that regulates the activity of enzymes such as elastase, excesses of which have been linked to chronic inflammatory disorders such as emphysema and chronic bronchitis. Inhibition of the appropriate MMP may thus potentiate the inhibitory activity of endogenous inhibitors of this type. Beeley, N. R. A. et al., supra.; Wahl, R. C. et al., *Annual Reports in Medicinal Chemistry* 25, 177–184 (1990).

High levels of mRNA corresponding to stromelysin have been observed in atherosclerotic plaques removed from heart transplant patients. Henney, A. M., et al., *Proc. Natl. Acad. Sci.* 88, 8154–8158 (1991). It is submitted that the role of stromelysin in such plaques is to encourage rupture of the connective tissue matrix that encloses the plaque. This rupture is in turn thought to be a key event in the cascade that leads to clot formation of the type seen in coronary thrombosis. MMP inhibition is thus a preventive measure for such thromboses.

Collagenase, stromelysin and gelatinase have been implicated in the destruction of the extracellular matrix of the cornea. This is thought to be an important mechanism of morbidity and visual loss in a number of ulcerative ocular diseases, particularly those following infection or chemical damage. Burns, F. R. et al., *Invest. Opthalmol. and Visual Sci.* 32, 1569–1575 (1989). The MMPs present in the eye during ulceration are derived either endogenously from infiltrating leucocytes or fibroblasts, or exogenously from microbes.

Collagenase and stromelysin activities have been identified in fibroblasts isolated from inflamed gingiva and the levels of enzyme have been correlated with the severity of the gingivitis observed. Beeley, N. R. A. et al., supra.; Overall, C. M. et al., *J. Periodontal Res.* 22, 81–88 (1987).

Excessive levels of gelatinase-B in cerebrospinal fluid has been linked with incidence of multiple sclerosis and other neurological disorders. Beeley, N. R. A. et al., supra.; Miyazaki, K. et al., *Nature* 362, 839–841 (1993). The enzyme may play a key role in the demyelination of neurons and the breakdown of the blood brain barrier that occurs in such disorders.

In addition, a recent study indicates that MMP-12 is required for the development of cigarette smoke-induced emphysema in mice. *Science*, 277, 2002 (1997).

Apart from the role of these potentially very destructive enzymes in pathology, the MMPs play an essential role in cell regrowth and turnover in healthy tissue. Broad-spectrum inhibition of the MMPs in the clinical setting results in musculoskeletal stiffness and pain. H. S. Rasmussen and P. P. McCann, *Pharmacol. Ther.*, 75, 69–75 (1997). This side effect and others associated with broad-spectrum inhibition may be enhanced in chronic administration. Thus, it would be advantageous to provide selective MMP inhibitors.

Molecules that have been identified as inhibiting the activity of matrix metalloproteinases include cyclic and heterocyclic N-substituted alpha-imino hydroxamic and carboxylic acids, such as those described in EP 0861236, incorporated herein by reference. Current processes for preparing these types of molecules, however, suffer from a number of drawbacks in that, for example, they have a high number of steps and produce a relatively low yield of product. In addition, the prior art processes typically use carcinogenic intermediates such as nitrobiphenyls, which lead to racemates or partly racemized compounds that require subsequent separation of the enantiomers. Further, the intermediates used often have to be purified by column chromatography, which is not amenable to the mass production levels required by pilot plant or production operations. Accordingly, there is a need in the art for a process for preparing cyclic and heterocyclic N-substituted alpha-imino hydroxamic and carboxylic acids that does not suffer from such drawbacks.

SUMMARY OF THE INVENTION

The present invention is directed to a process for preparing a compound of Formula (I):

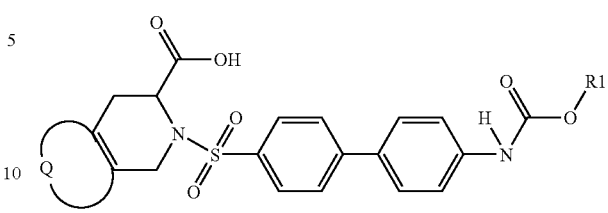

and/or all stereoisomeric forms of the compound of the Formula I and/or mixtures of these forms in any ratio, and/or a physiologically tolerated salt of the compound of the Formula I, wherein:

R1 is —$(C_1-C_{10})$-alkyl where alkyl is linear or branched; or —$(C_2-C_{10})$-alkenyl where alkenyl is linear or branched; or —$(C_2-C_{10})$-alkynyl where alkynyl is linear or branched; or —$(C_{1-C4})$-alkylphenyl; or —$(C_1-C_4)$-alkyl-$(C_3-C_7)$-cycloalkyl; or —$(C_3-C_7)$-cycloalkyl; or —$CH_2CF^3$; and Q is a radical selected from

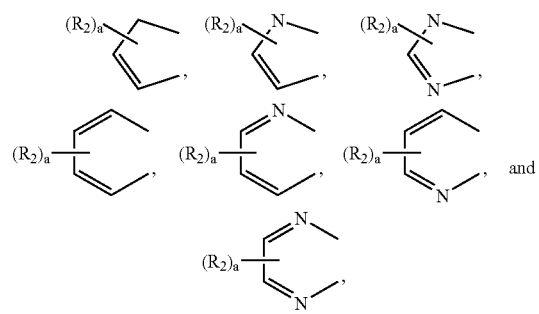

wherein $R_2$ is a hydrogen atom or —$(C_1-C_4)$-alkyl, and a is 0, 1, 2, or 3. The process comprises reacting a chlorosulfonylbiphenylcarbamate with a heterocyclic carboxylic acid that has been reacted with a silylating reagent, wherein the chlorosulfonylbiphenylcarbamate has a formula

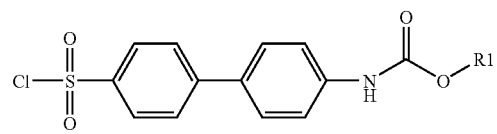

where R1 is as defined in Formula (I), and wherein the heterocyclic carboxylic acid has a formula

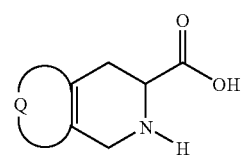

where Q is as defined in Formula (I).

The present invention is also directed to the following synthetic intermediates (Formulae II, III, and IV) that are useful in the preparation of the cyclic and heterocyclic N-substituted alpha-imino hydroxamic and carboxylic acids according to Formula (I):

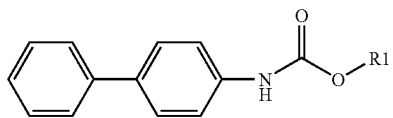

(II)

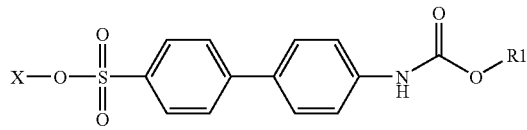

(III)

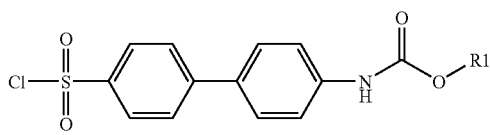

(IV)

wherein X is Li, Na, K, Rb and Cs and R1 is as previously defined.

DETAILED DESCRIPTION OF THE INVENTION

Definitions:

Unless otherwise stated, the following terms used in the specification and claims are defined for the purposes of this application and have the following meanings.

"$(C_1-C_{10})$-alkyl" refers to hydrocarbon radicals whose carbon chain is straight-chain or branched and contains from 1 to 10 carbon atoms, for example methyl, ethyl, propyl, isopropyl, butyl, isobutyl, tert-butyl, pentyl, isopentyl, neopentyl, hexyl, 2,3-dimethylbutyl, neohexyl, heptyl, octanyl, nonanyl or decanyl.

"$(C_2-C_{10})$-alkenyl" refers to hydrocarbon radicals whose carbon chains are straight-chain or branched and contain from 1 to 10 carbon atoms and, depending on the chain length, 1, 2 or 3 double bonds.

"$(C_2-C_{10})$-alkynyl" refers to hydrocarbon radicals whose carbon chains are straight-chain or branched and contain from 1 to 10 carbon atoms and, depending on the chain length, 1, 2 or 3 triple bonds.

"$(C_3-C_7)$-Cycloalkyl" radicals are, for example, compounds which are derived from 3- to 7-membered monocycles such as cyclopropyl, cyclobutyl, cyclopentyl, cyclohexyl or cycloheptyl.

"aqueous alkali metal salt solution" refers to solutions of water-soluble alkali metal salts, for example alkali metal halides such as NaCl, KCl, LiCl, RbCl or CsCl, or alkali metal sulfates such as $Na_2SO_4$, $K_2SO_4$, $Li_2SO_4$, $Rb_2SO_4$ or $Cs_2SO_4$. For example, from 10 g to 300 g of NaCl are dissolved at 25° C. in one liter of water.

"chlorinating reagent" refers to compounds which can be used to convert carboxylic acids, sulfonic acids or salts thereof to carbonyl chlorides or sulfonyl chlorides, for example $PCl_5$, $POCl_3$, $SOCl_2$, triphenylphosphine in $CCl_4$ or mixtures of the chlorinating reagents. Such reagents are described, for example, in R. C. Larock, Comprehensive Organic Transformations: a Guide to Functional Group Preparations, VCH Publishers, New York, Weinheim, 1999, p. 1929–1930.

"organic base" refers to organic amines, for example, quinoline, morpholine, piperidine, pyridine, triethylamine, picoline, lutidine. Preference is given to pyridine.

"aprotic organic solvent" refers to solvents that do not have a labile hydrogen such as, for example, chloroform, dichloromethane, pentane, heptane, hexane, tetrachloromethane, toluene, benzene, xylene, chlorobenzene, 1,2-dichloroethane, and trichloroethylene.

"organic solvent III" refers to solvents such as acetonitrile, dichloromethane, chloroform, tetrahydrofuran, toluene, dimethoxyethane, dioxane, and diethylene glycol dimethyl ether.

"pathology" of a disease means the essential nature, causes and development of the disease as well as the structural and functional changes that result from the disease processes.

"silylating agent" refers to compounds which are suitable for silylating carboxyl groups, described, for example, in T. W. Greene. P. G. M. Wuts, Protective Groups in Organic Chemistry, Wiley, N.Y., 1991, Chapter 5. Examples of silylating agents are N,O-bis(trimethylsilyl) acetamide or trimethylsilyl chloride or mixtures of the silylating agents.

"sulfonating reagent" refers to compounds as described, for example, in M. B. Smith and J. March, March's Advanced Organic Chemistry: Reactions, Mechanisms, and Structure, Wiley, N.Y. 2001, p. 702–704 and the literature cited there, for example chlorosulfonic acid, sulfuric acid, sulfuryl chloride, fuming sulfuric acid or sulfur trioxide or mixtures thereof.

Chemistry

The present invention is directed to a process for the preparation of cyclic and heterocyclic N-substituted alpha-imino hydroxamic and carboxylic acids according to Formula (I):

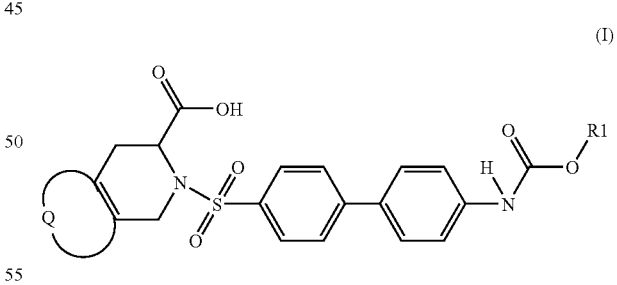

(I)

and/or all stereoisomeric forms of the compound of the Formula (I) and/or mixtures of these forms in any ratio, and/or a physiologically tolerated salt of the compound of the Formula (I), wherein:

R1 is —$(C_1-C_{10})$-alkyl where alkyl is linear or branched; or —$(C_2-C_{10})$-alkenyl where alkenyl is linear or branched; or —$(C_2-C_{10})$-alkynyl where alkynyl is linear or branched; or —$(C_1-C_4)$-alkylphenyl; or —$(C_1-C_4)$-alkyl-$(C_3-C_7)$-cycloalkyl; or —$(C_3-C_7)$-cycloalkyl; or —$CH_2CF_3$; and Q is a radical selected from

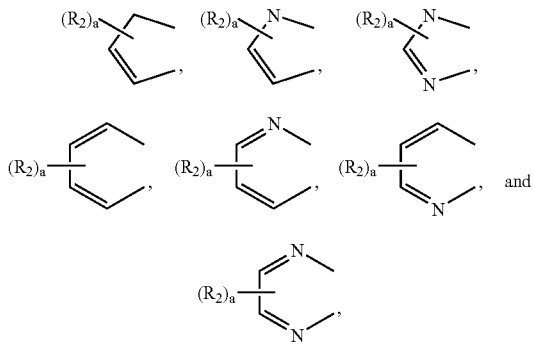

wherein $R_2$ is a hydrogen atom or —$(C_1$–$C_4)$-alkyl, and a is 0, 1, 2, or 3. The process comprises reacting a chlorosulfonylbiphenylcarbamate with a heterocyclic carboxylic acid that has been reacted with a silylating reagent, wherein the chlorosulfonylbiphenylcarbamate has a formula

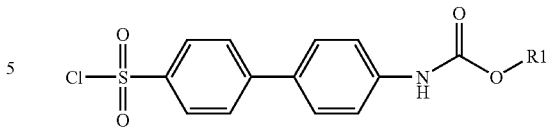

where R1 is as defined in Formula (I), and wherein the heterocyclic carboxylic acid has a formula

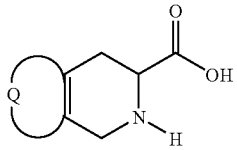

where Q is as defined in Formula (I).

According to the present invention, the process for preparing the cyclic and heterocyclic N-substituted alpha-imino hydroxamic and carboxylic acids according to Formula (I) and the novel intermediates (II), (III), and (IV) that are useful for preparing such compounds is outlined in Reaction Scheme I:

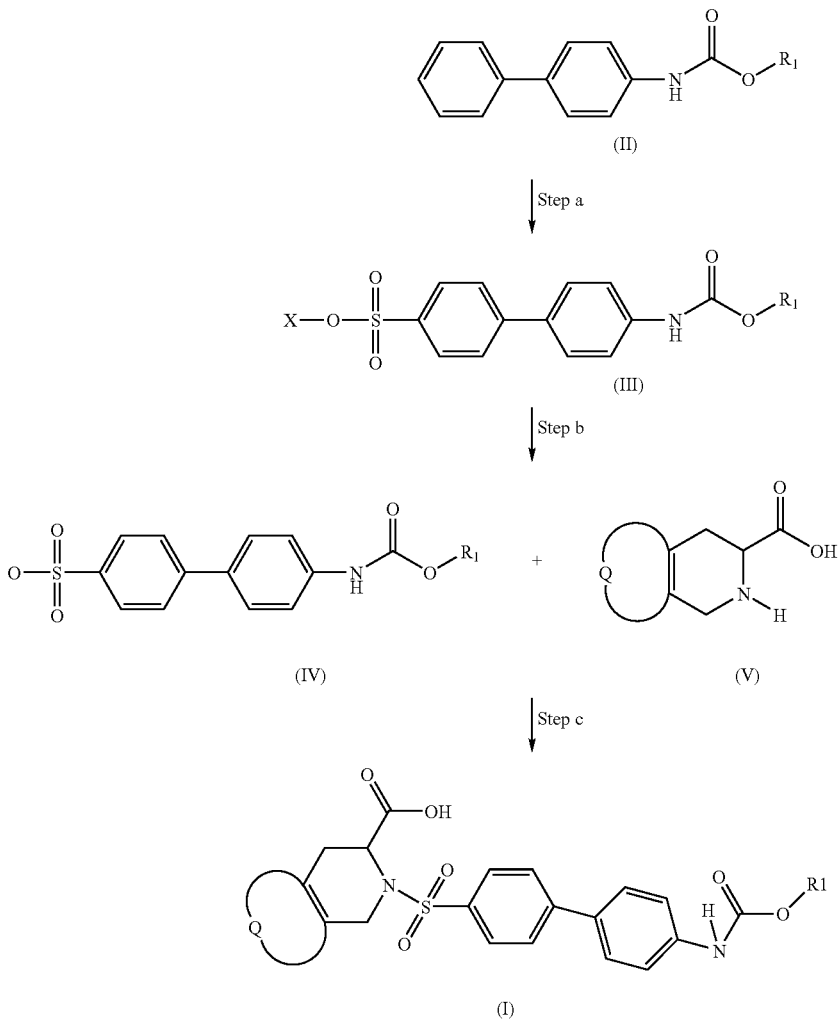

In Reaction Scheme 1, all substituents are as previously defined.

In step a, a compound of Formula (II) is reacted with a sulfonating reagent to give a compound of Formula (III). The compounds of Formula (II) are either known or can be prepared, for example, by reacting biphenyl 4-isocyanate with the appropriate alcohol R1-OH in an aprotic organic solvent. The resulting compound of Formula (III) is typically recovered by precipitation techniques known in the art such as, for example, using an aqueous alkali metal salt solution followed by filtration.

In one embodiment of the invention, the reaction of step a is typically carried out in an aprotic organic solvent with stirring at a temperature of from about −40° C. to about 20° C., preferably from about −30° C. to about 20° C. The reaction is typically carried out for from about 0.5 to about 6 hours depending on the composition of the mixture and the specific temperature range. Preferably, the aprotic solvent in step a is chloroform, dichloromethane, pentane, heptane, hexane, tetrachloromethane, benzene, toluene, xylene, chlorobenzene, 1,2-dichloroethane, or trichloroethylene, or mixtures thereof.

According to one embodiment of the invention, preferably from about 0.1 to about 5 mol of a compound of Formula (II) is dissolved in 1000 ml of organic solvent. More preferably, about 1 mol to about 10 mol and, most preferably, from about 1 mol to about 3 mol of the sulfonating reagent for about 1 mol of a compound of Formula (II) is used in the reaction of step a.

Preferred sulfonating reagents include chlorosulfonic acid, sulfuric acid, sulfuryl chloride, fuming sulfuric column, sulfur trioxide, or mixtures thereof.

The resulting compound of Formula (III) is typically recovered by precipitation using an aqueous alkali metal salt solution. For the precipitation, from about 0.11 to about 10.1 of the aqueous alkali metal salt solution is typically used based on 1 l of the reaction mixture with a compound of Formula (II). Preferably, the concentration of the alkali metal salt solution is from about 10 to about 300 g per liter of water, and the total amount of alkali metal salt is at least about 1 mol for about 1 mol of the organic compound. Preferred alkali metal salts include NaCl, KCl, LiCl, RbCl, CsCl, $Na_2SO_4$, $K_2SO_4$, $Li_2SO_4$, $Rb_2SO_4$, and $Cs_2SO_4$.

The compound of Formula (III) is then typically removed from the reaction mixture by filtration means well known to those skilled in the art. The filtration is typically effected, for example, using a Büchner suction filter and a suction flask with application of reduced pressure or using a pressure filter.

In step b, a compound of Formula (III) is reacted with a chlorinating reagent to give a compound of Formula (IV). Preferably, from about 0.2 to about 10 mol of a compound of Formula (III) is dissolved in about 1000 ml of an aprotic organic solvent. Preferred aprotic organic solvents for use in step b according to preferred embodiments of the invention include chloroform, dichloromethane, pentane, heptane, hexane, tetrachloromethane, toluene, benzene, xylene, chlorobenzene, 1,2-dichloroethane, trichloroethylene, and mixtures thereof.

In preferred a preferred embodiment of the invention, about 0.1 mol to about 5 mol and, more preferably, from about 0.1 mol to about 1 mol of the organic base is used for about 1 mol of a compound of Formula (III). Even more preferred is the use of from about 1 mol to about 5 mol and, in particular, from about 1 mol to about 2 mol of the chlorinating reagent for about 1 mol of a compound of Formula (III).

Preferred chlorinating reagents include $PCl_5$, $POCl_3$, $SOCl_2$, triphenylphosphine in $CCl_4$ or mixtures of these reagents.

The reaction of the compound of Formula (III) with the chlorinating reagent exemplified by step b is typically carried out in the aprotic organic solvent with stirring in the presence of an organic base at a temperature from about 10° C. to about 150° C., and preferably from about 30° C. to about 100° C. The reaction time for step b typically takes from about 0.5 to about 6 hours, depending on the composition of the mixture and the specific temperature range. A compound of Formula (IV) is then removed from the reaction mixture by aqueous workup and extraction with an aprotic organic solvent.

In step c, a compound of Formula (V) is chemically converted to a compound of Formula (I) by reaction with a compound of Formula (IV). In preferred embodiments of the invention, this is typically accomplished by first silylating the compound of Formula (V) by reacting it with a silylating agent to protect the carboxylic group. In preferred embodiments of the invention, this reaction is typically carried out in an organic solvent III with stirring at a temperature from about 10° C. to about 150° C. and preferably from about 30° C. to about 100° C. The reaction typically requires from about 0.5 to about 10 hours for completion, depending on the composition of the mixture and specific temperature range.

In one preferred embodiment of the invention, preferably from about 0.1 to about 10 mol of a compound of Formula (V) is dissolved in about 1000 ml of the organic solvent III. In more preferred embodiments, from about 0.5 mol to about 2 mol and, in particular, from about 0.9 mol to about 1.1 mol of a compound of Formula (V) is present for about 1 mol of a compound of Formula (IV). Preferably, from about 1 mol to about 5 mol and, in particular, from about 2 mol to about 2.5 mol of the silylating agent is used for about 1 mol of a compound of Formula (V).

Preferred silylating agents include N,O-bistrimethylsilylacetamide or trimethylsilyl chloride.

Preferred organic solvents III for use in step c include acetonitrile, dichloromethane, chloroform, tetrahydrofuran, toluene, dimethoxyethane, dioxane, diethylene glycol dimethyl ether, or mixtures thereof.

A compound of Formula (IV) is then reacted with the silylated compound of Formula (V) to give a compound of Formula (I). According to preferred embodiments of the invention, this reaction is typically carried out in the same reaction mixture used to silylated the compound of Formula (V) and under the same temperature conditions for the same length of time. The compound of Formula (I) is then typically removed from the reaction mixture by aqueous workup and extraction with an organic solvent.

The end products of each reaction are generally determined by $^1H$ NMR at 400 MHz in DMSO-D6.

The following examples present typical syntheses as described in Reaction Scheme A. These examples are understood to be illustrative only and are not intended to limit the scope of the present invention in any way. As used herein, the following terms have the indicated meanings: "g" refers to grams; "mmol" refers to millimols; "mL" refers to milliliters; "bp" refers to boiling point; "mp" refers to melting point; "° C." refers to degrees Celsius; "mm Hg" refers to millimeters of mercury; "μL" refers to microliters; "μg" refers to micrograms; and "μM" refers to micromolar.

EXAMPLES

The present invention is further exemplified, but not limited by, the following examples that illustrate the preparation of compounds of Formula (I) and intermediates thereof according to the present invention.

Example 1

Preparation of isopropyl biphenyl-4-ylcarbamate

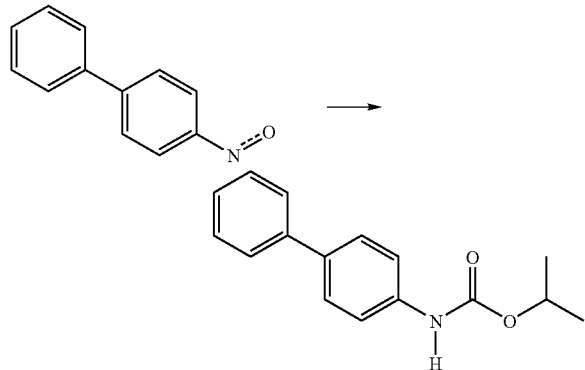

230 ml of isopropanol (3 mol) were added at 20° C. within 2 minutes (min.) to a suspension of 4-biphenyl isocyanate (204 g, purity 96.6%, 1.0 mol) in 1.2 liters (l) of toluene. The internal temperature was, if appropriate, kept below 30° C. by gentle cooling using an ice bath. After 75 min, the mixture was heated to 50° C. and subsequently left to cool with stirring to 20° C. within 2 hours (h), in the course of which the product crystallized out. Subsequently, the mixture was cooled in an ice bath and the precipitated crystals were filtered off with suction and washed with toluene. 188 g of crystalline product were obtained. The filtrate was concentrated under reduced pressure and the residue crystallized in toluene (200 ml). In this way, a further 59 g of product were obtained.

Total yield: 247 g (97%) of isopropyl biphenyl-4-ylcarbamate, colorless crystals, melting point (m.p.) 138.5° C. to 139° C., $^1$H NMR (400 MHz, CDCl$_3$): δ=1.31 (d, J=6 Hz, 6H), 5.04 (heptet, J=6 Hz, 1H), 6.61 (bs, 1H), 7.31 (t, J=7.5H, 1H), 7.41 (d, J=8 Hz, 2H), 7.45 (d, J=9 Hz, 2H), 7.55 (t, J=8 Hz, 2H) ppm. Analysis: C$_{16}$H$_{17}$NO$_2$ (255.32): calculated C, 75.27; H, 6.71; N, 5.49; found C, 75.27; H, 6.61; N, 5.57.

Example 2

Preparation of 4'-isopropoxycarbonylaminobiphenyl-4-sulfonic acid sodium salt

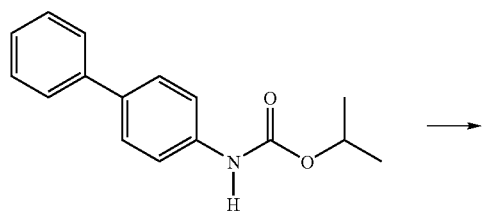

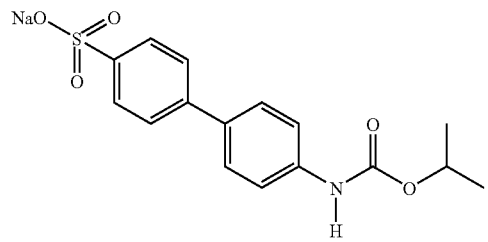

A suspension of isopropyl biphenyl-4-ylcarbamate (256 g, 1 mol) in dichloromethane (2000 ml) was cooled to −10° C. and chlorosulfonic acid (350 g, 200 ml, 3 mol) was added dropwise with stirring within 25 min with gentle cooling using a dry ice-methanol bath. The internal temperature was kept below −4° C. Subsequently, the dry ice-methanol bath was replaced by an ice bath and the mixture was stirred at from 3° C. to 14° C. for 1.5 h. Afterward, chlorosulfonic acid (175 ml, 2.6 mol) was again added at from 2° C. to 3° C., the mixture was stirred again for 30 min and then worked up. To this end, a mixture of ice (5 kg), methylene chloride (1000 ml) and concentrated NaCl solution (1300 ml) was initially charged under vigorous stirring and the reaction mixture was added slowly. The precipitated solid was filtered off with suction and dried at 45° C. under reduced pressure. 329 g (92%) of 4'-isopropoxycarbonylaminobiphenyl-4-sulfonic acid sodium salt were obtained as a white, crystalline powder, m.p.>260° C., $^1$H NMR (400 MHz, DMSO-D6): δ=1.27 (d, J=6 Hz, 6H), 4.91 (heptet, J=6 Hz, 1H), 7.54–7.66 (sh, 8H), 9.66 (bs, 1H) ppm. Analysis: C$_{16}$H$_{16}$NNaO$_5$S (357.36): calculated C, 53.78; H, 4.51; N, 3.92; Na, 6.43; found C, 54.13; H, 4.39; N, 4.17; Na, 5.9.

Example 3

Preparation of isopropyl(4'-chlorosulfonylbiphenyl-4-yl)carbamate

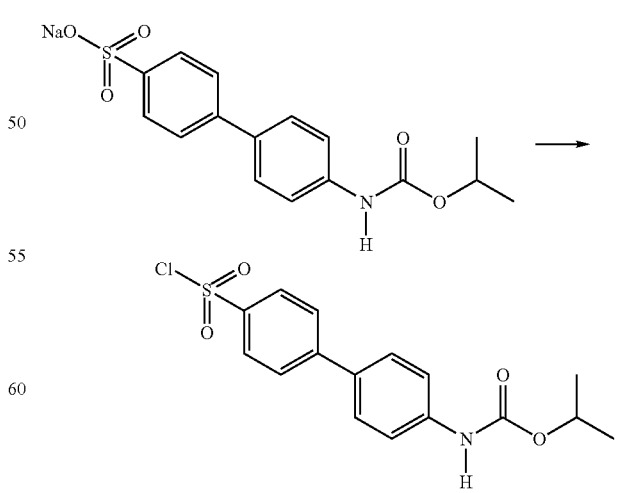

A mixture of 4'-isopropoxycarbonylaminobiphenyl-4-sulfonic acid sodium salt (283 g, 0.79 mol), toluene (700 ml)

and pyridine (35 ml, 0.43 mol) was stirred vigorously at RT and POCl₃ (215 ml) was slowly added dropwise such that the internal temperature was kept between 30° C. and 45° C. Subsequently, PCl₅ (100 g) was added at 35° C. in about 6 portions and the mixture was heated to 60° C. within 30 min. Afterward, further PCl₅ (100 g) was added at 70° C. within 15 min and the mixture was left to stir without further heating for 1 h. In this time, the internal temperature fell to about 30° C. The mixture was diluted with dichloromethane (500 ml) and then worked up. To this end, a mixture of ice-water (5 kg), saturated NaCl solution (1000 ml) and dichloromethane (1000 ml) was initially charged with vigorous stirring and the reaction mixture was slowly added dropwise. In this time, the temperature was kept at from 15° C. to 25° C. by adding ice (2 kg). Subsequently, stirring was continued for 1 h, in the course of which the temperature was allowed to rise up to 30° C. The phases were separated and the aqueous phase was extracted twice using dichloromethane (1500 ml). The combined organic phases were reextracted using water (8000 ml), dried over Na₂SO₄ and concentrated by evaporation under reduced pressure. About 360 g of crude product were obtained as beige crystals. These were taken up in dichloromethane and filtered through a silica gel layer (15×30 cm, 70–200 µm), the layer was rinsed using dichloromethane and the filtrate was concentrated by evaporation. 270 g (96%) of isopropyl(4'-chlorosulfonylbiphenyl-4-yl)carbamate were obtained as yellow crystals.

¹H NMR (400 MHz, CDCl₃): δ=1.33 (d, J=6 Hz, 6H), 5.05 (heptet, J=6 Hz, 1H), 6.68 (bs, 1H), 7.53 (d, J=9 Hz, 2H), 7.59 (d, J=9 Hz, 2H), 7.88 (d, J=9 Hz, 2H), 8.08 (d, J=9Hz, 2H) ppm.

Example 4

Preparation of (R)-2-(4'-isopropoxycarbonylamino-biphenyl-4-sulfonyl)-1,2,3,4-tetrahydroisoquinoline-3-carboxylic acid

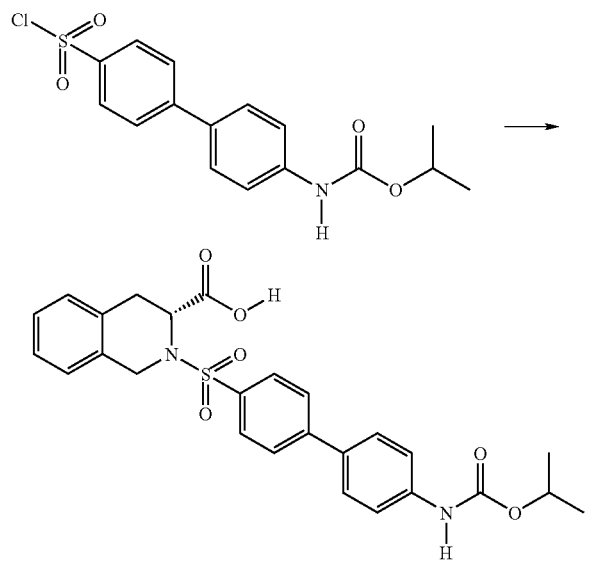

(R)-1,2,3,4-Tetrahydroisoquinoline-3-carboxylic acid (139 g, 0.78 mol) were suspended in anhydrous acetonitrile (3000 ml) under dry nitrogen and N,O-bis(trimethylsilyl)acetamide (334 g, 400 ml, 1.64 mol) were added at 20° C. with stirring within 5 min. The mixture was heated to reflux for 1.5 h and then allowed to cool to 74° C. Subsequently, isopropyl(4'-chlorosulfonylbiphenyl-4-yl)carbamate (277 g, 0.78 mol) were added with stirring in 8 portions within 10 min, in the course of which gas evolution was observed. The low-boiling trimethylsilyl chloride formed was distilled off and the mixture was then heated to reflux for a further 2.5 h. Subsequently, the mixture was cooled to RT and poured with vigorous stirring into a mixture of water (10 l), citric acid (80 g) and ethyl acetate (1500 ml), and the phases were separated. The aqueous phase was extracted twice using ethyl acetate (1000 ml each time) and the combined organic phases were reextracted with water (7 l). After drying over Na₂SO₄, the mixture was concentrated by evaporation under reduced pressure. 506 g of beige, crystalline crude product were obtained, which were purified by recrystallization from dichloromethane (1000 ml). Yield 316 g (78%) of (R)-2-(4'-isopropoxycarbonylaminobiphenyl-4-sulfonyl)-1,2,3,4-tetrahydroisoquinoline-3-carboxylic acid, colorless crystals, m.p. from 133° C. to 135° C. (softening), from 173° C. to –175° C. (melting with gas evolution).

¹H NMR (400 MHz, DMSO-d₆): δ=1.27 (d, J=6 Hz, 6H), 3.04 (dd, J=16 Hz, J₂6 Hz, 1H), 3.11 (dd, J₁=16 Hz, J₂=3 Hz, 1H), 4.49 (d, J=16 Hz, 1H), 4.61 (d, J=16 Hz, 1H), 4.85–4.95(sh, 2H), 7.15 (m, 4H), 7.59 (d, J=9 Hz, 1H), 7.67 (d, J=9 Hz, 1H), 7.81 (d, J=9 Hz, 1H), 7.86 (d, J=9 Hz, 1H), 9.74 (s, 1H), 12.86 (bs, 1H) ppm. Analysis: C₂₆H₂₆N₂O₆S (494.57): calculated C, 63.14; H, 5.30; N, 5.66; found C, 62.81, H, 5,57, N, 5.49.

Determination of the Enantiomeric Purity by HPLC on Chiral Phase:

Chiralpak AD-H/39 250×4.6, eluent: 8:1:1 heptane/methanol/ethanol+1% NH₄OAc, retention time of [(R)-1,2,3,4-tetrahydroisoquinoline-3-carboxylic acid]=7.349 min (99.97%), retention time of [(S)-1,2,3,4-tetrahydroisoquinoline-3-carboxylic acid]=8.521 min (0.03%). Enantiomeric purity 99.94% ee.

What is claimed is:

1. A process for preparing a compound of Formula (I):

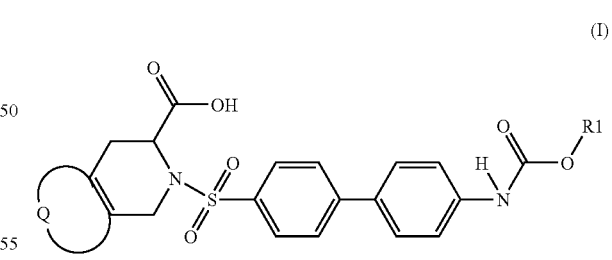

(I)

and/or all stereoisomeric forms of the compound of the Formula (I) and/or mixtures of these forms in any ratio, and/or a physiologically tolerated salt of the compound of the Formula (I), wherein:

R1 is —(C₁–C₁₀)-alkyl where alkyl is linear or branched; or —(C₂–C₁₀)-alkenyl where alkenyl is linear or branched; or —(C₂–C₁₀)-alkynyl where alkynyl is linear or branched; or —(C₁–C₄)-alkylphenyl; or —(C₁–C₄)-alkyl-(C₃–C₇)-cycloalkyl; or —(C₃–C₇)-cycloalkyl; or —CH₂CF₃; and Q is a radical selected from

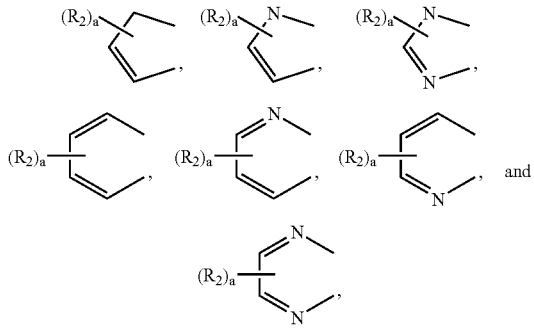

wherein $R_2$ is —($C_1$–$C_4$)-alkyl, and a is 0, 1, 2, or 3;
wherein said process comprises
a) reacting a heterocyclic carboxylic acid of Formula (V)

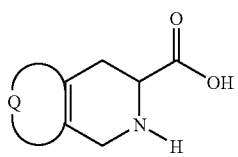

(V)

where Q is as defined in Formula (I), with a silylating reagent; and
b) reacting the product of step a) with chlorosulfonylbiphenylcarbamate of Formula (IV)

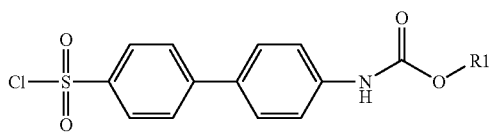

(IV)

where R1 is as defined in Formula (I).

2. The process of claim 1 wherein the chlorosulfonylbiphenylcarbamate of Formula (IV) is prepared by chlorinating a compound of Formula (III)

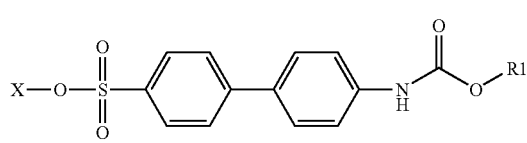

(III)

wherein R1 is as defined in Formula (I) and X is an alkali metal or hydrogen, with a chlorinating reagent.

3. The process of claim 2 wherein the compound of Formula (III) is prepared by sulfonating a compound of Formula (II)

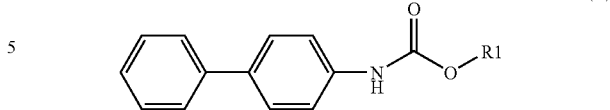

(II)

where R1 is as defined in Formula (III) with a sulfonating reagent and then reacting that product with an alkali metal salt solution.

4. The process of claim 3 wherein the sulfonating reagent is chlorosulfonic acid, sulfuric acid, sulfuryl chloride, fuming sulfuric acid or sulfur trioxide.

5. The process of claim 3 wherein the sulfonation is performed in an aprotic solvent.

6. The process of claim 5 wherein the aprotic solvent in sulfonation is selected from the group of consisting of chloroform, dichloromethane, pentane, heptane, hexane, tetrachloromethane, benzene, toluene, xylene, chlorobenzene, 1,2-dichloroethane, and trichloroethylene.

7. The process of claim 3 wherein the alkali metal salt solution is a solution of water-soluble alkali metal salts selected from the group consisting of $Na_2SO_4$, $K_2SO_4$, $Li_2SO_4$, $Rb_2SO_4$, $Cs_2SO_4$.

8. The process of claim 3 wherein the alkali metal salt solution is a solution of water-soluble alkali metal salts selected from the group consisting of NaCl, KCl, LiCl, RbCl, and CsCl.

9. The process of claim 3, wherein the sulfonating reagent is present in a ratio of about 1 mol to about 10 mol to 1 mol of a compound of Formula (II).

10. The process of claim 9, wherein the sulfonating reagent is present in a ratio of about 1 mol to about 3 mol to 1 mol of a compound of Formula (II).

11. The process of claim 2 wherein the chlorination is performed in an aprotic solvent.

12. The process of claim 11 wherein the aprotic solvent in chlorination is chloroform, dichloromethane, pentane, heptane, hexane, tetrachloromethane, toluene, benzene, xylene, chlorobenzene, 1,2-dichloroethane or trichloroethylene.

13. The process of claim 2 wherein the chlorinating reagent is $PCl_5$, $POCl_3$, $SOCl_2$, triphenylphosphine in $CCl_4$, or mixtures thereof.

14. The process of claim 2, wherein the chlorinating reagent is present in a ratio of about 1 mol to about 5 mol to 1 mol of a compound of Formula (III).

15. The process of claim 14, wherein the chlorinating reagent is present in a ratio of about 1 mol to about 2 mol to 1 mol of a compound of Formula (III).

16. The process of claim 1 wherein the silylating reaction is performed in a solvent slected from acetonitrile, dichloromethane, chloroform, tetrahydrofuran, toluene, dimethoxyethane, dioxane or diethylene glycol dimethyl ether, or a mixture thereof.

17. The process of claim 1 wherein the silylating reagent is N,O-bis(trimethylsilyl)acetamide, trimethylsilyl chloride, or a mixture thereof.

18. The process of claim 1, wherein a compound of Formula (V) is present in a concentration of about 0.5 mol to about 2 mol to 1 mol of a compound of Formula (IV).

19. The process of claim 18, wherein a compound of Formula (V) is present in a concentration of about 0.9 mol to about 1.1 mol to about 1 mol of a compound of Formula (IV).

20. The process of claim 1, wherein the silylating reagent is present in a concentration of about 1 mol to about 5 mol to about 1 mol of a compound of Formula (V).

21. The process of claim 20, wherein the silylating reagent is present in a concentration of about 2 mol to about 2.5 mol to about 1 mol of a compound of Formula (V).

22. A compound of Formula (III)

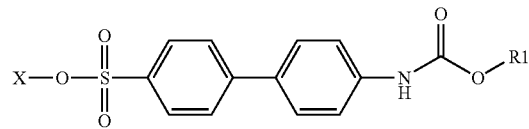

wherein:
R1 is —$(C_1$–$C_{10})$-alkyl where alkyl is linear or branched, or —$(C_2$–$C_{10})$-alkenyl where alkenyl is linear or branched, or —$(C_2$–$C_{10})$-alkynyl where alkynyl is linear or branched, or —$(C_1$–$C_4)$-alkylphenyl, or —$(C_1$–$C_4)$-alkyl-$(C_3$–$C_7)$-cycloalkyl, —$(C_3$–$C_7)$-cycloalkyl or —$CH_2CF_3$; and X is Li, Na, K, Rb, and Cs.

23. A Compound of the Formula IV

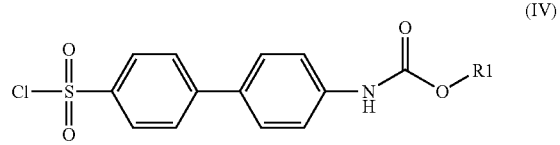

wherein:
R1 is —$(C_1$–$C_{10})$-alkyl where alkyl is linear or branched, or —$(C_2$–$C_{10})$-alkenyl where alkenyl is linear or branched, —$(C_2$–$C_{10})$-alkynyl where alkynyl is linear or branched, —$(C_1$–$C_4)$-alkylphenyl, —$(C_1$–$C_4)$-alkyl-$(C_3$–$C_7)$-cycloalkyl, —$(C_3$–$C_7)$-cycloalkyl or —$CH_2CF_3$.

* * * * *